(12) United States Patent
Larue et al.

(10) Patent No.: US 8,486,652 B2
(45) Date of Patent: Jul. 16, 2013

(54) METHOD FOR THE IN VITRO DIAGNOSIS OF STROKE

(75) Inventors: Catherine Larue, Vaucresson (FR); Johann Guegan, Rueil Malmasion (FR); Isabelle Giuliani, Borville (FR)

(73) Assignee: Bio-Rad Innovations, Marnes la Coquette (FR)

( * ) Notice: Subject to any disclaimer, the term of this patent is extended or adjusted under 35 U.S.C. 154(b) by 0 days.

(21) Appl. No.: 13/147,007

(22) PCT Filed: Jan. 30, 2009

(86) PCT No.: PCT/IB2009/051978
§ 371 (c)(1),
(2), (4) Date: Oct. 24, 2011

(87) PCT Pub. No.: WO2010/086697
PCT Pub. Date: Aug. 5, 2010

(65) Prior Publication Data
US 2012/0028824 A1    Feb. 2, 2012

(51) Int. Cl.
*C12Q 1/42* (2006.01)
(52) U.S. Cl.
USPC .......................................................... 435/21
(58) Field of Classification Search
USPC .................................................. 435/21; 506/9
See application file for complete search history.

(56) References Cited

U.S. PATENT DOCUMENTS

2004/0219509 A1 * 11/2004 Valkirs et al. ...................... 435/4
2005/0064511 A1 * 3/2005 Buechler et al. ................ 435/7.1
2005/0255484 A1 * 11/2005 Valkirs et al. ...................... 435/6
2011/0263821 A1 * 10/2011 Bergmann et al. ............ 530/350
2011/0312517 A1 * 12/2011 Giuliani et al. ................... 506/9

FOREIGN PATENT DOCUMENTS

WO    WO 2004/014952    *    2/2004
WO    WO 2005/029088 A2    3/2005

OTHER PUBLICATIONS

Allard L. et al. PARK7 and NDKA as Plasma Markers for the Early Diagnosis of Stroke. Clinical Chemistry 51:2043-2051, 2005.*
Seferian K. et al. The BNP Precursor is the Major Immunoreactive Form of BNP in Patients with Heart Failure. Clinical Chemistry 53:866-873, 2007.*
Allard L. et al. 2005 "PARK7 and nucleoside diphosphate kinase A as plasma markers for the early diagnosis of stroke" *Clinical Chemistry* 51: 2043-2051.
Giuliani I. et al. 2006 "Assay for measurement of intact B-type natriuretic peptide prohormone in blood" *Clinical Chemistry* 52: 1054-1061.
Lynch, J.R. et al. 2004 "Novel diagnostic test for acute stroke" *Stroke* 35: 57-63.

* cited by examiner

*Primary Examiner* — Ralph Gitomer
(74) *Attorney, Agent, or Firm* — Knobbe Martens Olson & Bear LLP

(57) ABSTRACT

A method for the in vitro diagnosis of stroke and transient ischemic attack (TIA) in an individual, including the following steps: (a) measuring the level of proBNP(1-108), or of fragments of proBNP(1-108) including a RAPRSP sequence (SEQ ID NO: 1), in a biological sample of the individual; (b) measuring the level of nucleoside diphosphate kinase A (NDKA) in a biological sample of the individual; (c) comparing the level of proBNP(1-108), or of fragments of proBNP(1-108), and the level of NDKA, with one or several cut-off values; and (d) determining therefrom whether a stroke or a TIA has occurred in the individual.

14 Claims, No Drawings

SEQUENCE LISTING

```
<160> NUMBER OF SEQ ID NOS: 5

<210> SEQ ID NO 1
<211> LENGTH: 6
<212> TYPE: PRT
<213> ORGANISM: Homo sapiens

<400> SEQUENCE: 1

Arg Ala Pro Arg Ser Pro
1               5

<210> SEQ ID NO 2
<211> LENGTH: 7
<212> TYPE: PRT
<213> ORGANISM: Homo sapiens

<400> SEQUENCE: 2

Phe Gly Arg Lys Met Asp Arg
1               5

<210> SEQ ID NO 3
<211> LENGTH: 32
<212> TYPE: PRT
<213> ORGANISM: Homo sapiens

<400> SEQUENCE: 3

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
```

```
<210> SEQ ID NO 4
<211> LENGTH: 108
<212> TYPE: PRT
<213> ORGANISM: Homo sapiens

<400> SEQUENCE: 4

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 5
<211> LENGTH: 152
<212> TYPE: PRT
<213> ORGANISM: Homo sapiens

<400> SEQUENCE: 5

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150
```

METHOD FOR THE IN VITRO DIAGNOSIS OF STROKE

FIELD OF THE INVENTION

The present invention relates to methods and kits for the in vitro diagnosis of stroke.

BACKGROUND OF THE INVENTION

Stroke, also known as cerebrovascular accident (CVA), is one of the leading causes of mortality and morbidity with an estimated 700,000 patients diagnosed with stroke each year. Stroke currently ranks third in the cause of death in the U.S.A.

The term "stroke" encompasses two widely different clinical settings which it is of the utmost importance to distinguish. Ischemic stroke is thus usually caused by the blockage of blood vessels and is best treated by clot dissolving agents, such as t-PA, within three hours of symptom onset. In contrast, hemorrhagic stroke is caused by bleeding into the brain which forbids any treatment by anti-clotting agents, which could prove fatal.

Transient ischemic attack (TIA, often colloquially referred to as "mini stroke") is caused by the changes in the blood supply to a particular area of the brain, resulting in brief neurologic dysfunction that persists, by definition, for less than 24 hours; if symptoms persist then it is categorized as a stroke (see e.g. Transient Ischemic Attacks: Stroke (CVA): Merck Manual Home Edition). Patients diagnosed with a TIA are sometimes said to have had a warning for an approaching stroke. If the time period of blood supply impairment lasts more than a few minutes, the nerve cells of that area of the brain die and cause permanent neurologic deficit. One third of the people with TIA later have recurrent TIAs and one third have a stroke due to permanent nerve cell loss (Transient ischemic attack Mount Sinai Hospital, New York). Therefore, the identification of TIA is beneficial because these patients are at increased risk of future stroke.

The diagnosis of stroke, and the segmentation between ischemic and hemorrhagic stroke, in patients which present with symptoms indicative of stroke, such as sudden numbness or blindness, confusion, severe headaches, slurred speech, and partial paralysis, currently essentially relies on computed tomography (CT). CT, however, is not completely satisfying since it has an estimated sensitivity of less than 26% in diagnosing acute stroke (Chalela et al. (2007) *Lancet* 369:293-298), which is linked to a very poor performance in detecting ischemic stroke, with less than 33% sensitivity (Reynolds et al. (2003) *Clin. Chem.* 49:1733-1739). Magnetic resonance imaging (MRI) has been shown to be superior to CT in diagnosing acute stroke (84% sensitivity, Chalela et al. (2007) *Lancet* 369:293-298), and particularly ischemic stroke. However MRI scanners are costly equipments and are not always available in the emergency room.

Accordingly there is still the need for alternative or complementary methods, in particular to CT, for diagnosing stroke and TIA.

In this respect, biochemical markers have been suggested as an aid in detecting stroke, in particular in view of the early detection of ischemic stroke.

S-100b (a marker of astrocytic activation) and neuron-specific enolase (NSE) are among the best characterized such markers (Jauch et al. (2006) *Stroke* 37:2508-2513). Heart-type fatty acid binding protein (H-FABP) has also been considered as a promising marker (Lescuyer et al. (2005) *Mol. Diagn.* 9:1-7). However, it seems that the discriminatory power offered by these markers individually is not sufficient to be of clinical value.

It has thus been suggested to use panels combining several markers, such as S-100b, the B-type neurotrophic growth factor (BNGF), the von Willebrand factor (vWF), matrix metalloproteinase-9 (MMP-9) and monocyte chemotactic protein-1 (MCP-1), for diagnosing ischemic stroke (Reynolds et al. (2003) *Clin. Chem.* 49:1733-1739). Indeed, this panel was shown to provide a sensitivity of 92% at 93% specificity for ischemic stroke sample within 6 hours from symptom onset. Within 3 hours from onset however, sensitivity is of only 87%, which might be due to a too low individual sensitivity/specificity of the markers. Besides, measuring the level of 5 different markers might be seen as cumbersome, especially in the emergency room.

Accordingly, there is still the need for alternative marker panels to be used as such or to improve other multi-marker panels, either by increasing sensitivity/specificity or by enabling reducing the number of markers which levels have to be measured in panels.

proBNP(1-108), a precursor protein of 108 amino acids, is cleaved in vivo to yield (i) Brain Natriuretic Peptide (also referred to as BNP(32) or simply BNP), which consists of the 32 C-terminal amino acids of proBNP(1-108) and (ii) NT-proBNP, which consists of the 76 N-terminal amino acids of proBNP(1-108) (Giuliani et al. (2006) Clinical Chemistry 52:1054-61). Biologically, BNP is a blood pressure regulatory agent which is released mainly from the left cardiac ventricle in response to volume expansion and pressure overload. proBNP(1-108) has been shown to be circulating in patients with severe heart failure (Hammerer-Lercher et al. (2008) Clinical Chemistry 54:5).

Nucleoside Diphosphate Kinase A (NDKA) has been shown to have a sensitivity of 70% and a specificity of 90% for stroke detection at a cut-off of 22 ng/μl as measured in the plasma of patients (Allard et al. (2005) Clin. Chem. 51:2043-2051).

SUMMARY OF THE INVENTION

The present invention arises from the unexpected finding, by the inventors, that proBNP(1-108) had a high discriminatory power (e.g. 90% sensitivity and 85% specificity) in stroke detection.

Thus, the present invention relates to a method for the in vitro diagnosis of stroke and Transient ischemic attack (TIA) in an individual, comprising the following steps:

(a) measuring the level of proBNP(1-108), or of fragments of proBNP(1-108) comprising a RAPRSP sequence (SEQ ID NO: 1), in a biological sample of the individual;

(b) measuring the level of nucleoside diphosphate kinase A (NDKA) in a biological sample of the individual;

(c) comparing the level of proBNP(1-108), or of fragments of proBNP(1-108), and the level of NDKA, with one or several cut-off values;

(d) determining therefrom whether a stroke or a TIA has occurred in the individual.

In another embodiment of the invention, the above-defined method further comprises measuring the level of at least one marker of cardiovascular diseases.

The present invention also relates to a kit for diagnosing stroke, comprising:

at least one antibody suitable for detecting proBNP(1-108), or of fragment of proBNP(1-108) which comprise a RAPRSP sequence (SEQ ID NO: 1); and optionally at least one callibrator comprising proBNP(1-108), or of fragment of proBNP(1-108) which comprise a RAPRSP sequence (SEQ ID NO: 1), at least at a concentration of 1 pg/ml; and at least one antibody suitable for detecting NDKA; and optionally at least one calibrator comprising NDKA, at least at a concentration of 7 ng/ml.

The present invention also relates to the use of:

proBNP(1-108), or of fragments of fragment of proBNP (1-108) which comprise a RAPRSP sequence (SEQ ID NO: 1), and

NDKA, for the in vitro diagnosis of stroke or TIA.

Deposit of Microorganism

The following microorganisms have been deposited in accordance with the terms of the Budapest Treaty with the COLLECTION NATIONALE DE CULTURES DE MICRO-ORGANISMS (CNCM), on the dates indicated:

| Microorganism | Accession No. | Date |
|---|---|---|
| Hybridoma Cell Line (3D4) | CNCM I-3073 | Jul. 31, 2003 |
| Hybridoma Cell Line (20G7-15/03/2007) | CNCM I-3746 | Aug. 13, 2007 |

These deposits were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for a period of at least five years after the most recent request for the furnishing of a sample of the deposited microorganism, and in any case for a period of at least thirty (30) years from the date of deposit for the enforceable life of the patent, whichever period is longer. The deposit will be made available by CNCM under the terms of the Budapest Treaty, and subject to an agreement between Applicant and CNCM which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strain is not to be construed as a license to practice the invention in contravention of the rights granted under the authority of any government in accordance with its patent laws.

DETAILED DESCRIPTION OF THE INVENTION

As intended herein "diagnosing" or establishing a "diagnosis" relates to determining if a stroke has occurred in an individual.

As intended herein "stroke" relates to all cerebrovascular accidents. In particular, the term "stroke" encompasses acute and chronic stroke as well as ischemic and hemorrhagic stroke.

Ischemic stroke is characterized by a partial or total occlusion of cerebral vessels which may lead to infarction and necrosis of cerebral tissues supplied by these vessels. In transient ischemic attack (TIA) the occlusion ceases spontaneously causing a dysfunction which lasts for no more than 24 hours.

Hemorrhagic stroke is characterized by an intracerebral haemorrhage generally from cerebral vessel rupture.

Preferably, the stroke according to the invention is selected from the group consisting of an ischemic stroke, a hemorrhagic stroke, or a transient ischemic attack (TIA). More preferably, the stroke as intended herein is acute ischemic stroke.

Advantageously, the method of the invention provides for early stroke diagnosis. Early stroke diagnosis is of particular importance in the case of ischemic stroke, since it is usually estimated that treating the occluded vessels within 3 hours of stroke symptoms onset will prevent most irreversible cerebral damages. Accordingly, it is preferred that the above defined step (a) is implemented within 6 hours, more preferably within 3 hours, and most preferably within 2 hours, after the onset of at least one symptom indicative of stroke in the individual.

The symptoms indicative of stroke are well known to one of skill in the art and notably encompass sudden numbness or blindness, confusion, severe headaches, slurred speech, and partial paralysis.

The individual is preferably a human.

"proBNP(1-108)" relates to the precursor BNP(32) and of NT-proBNP. As intended herein "proBNP(1-108)" encompasses all its natural variants, however it is preferred that proBNP(1-108) is represented by SEQ ID NO: 4.

In vivo, proBNP(1-108) is often partially truncated, in particular it is deleted of one or more amino acids on the N-terminal side or optionally on the C-terminal side, for instance by circulating proteases, to form so-called "proBNP (1-108) fragments". An example of such a proBNP(1-108) fragment, the proBNP(3-108) fragment produced by cleavage by a dipeptidase, is described in Lam et al. (2007) J. Am. Coll. Cardiol. 49:1193-1202. It is believed that it is not only proBNP(1-108) which is of diagnosis value but also its various natural fragments. Accordingly, the present invention not only relies on measuring the level of proBNP(1-108) but also the level of fragments of proBNP(1-108).

The expression "proBNP(1-108)" and "fragments of proBNP(1-108)" also include any polypeptide having been subjected to at least one post-translational modification, such as phosphorylation, glycosylation or the like. For example, Schellenberger et al. (2006) Arch. Biochem. Biophys. 51:160-6 have shown that proBNP(1-108) is a glycoprotein which is O-glycosylated either entirely or in part.

As intended herein the fragments of proBNP(1-108) comprise the RAPRSP sequence (SEQ ID NO: 1). This RAPRSP sequence harbours the site of proBNP(1-108) which is cleaved in vivo to yield NT-proBNP and BNP(32). As such, the RAPRSP is specific of proBNP(1-108) and cannot be found in BNP(32) nor in NT-proBNP, which are thus excluded from the definition of the fragments of proBNP(1-108) according to the invention.

It is further preferred that the fragments of proBNP(1-108) according to the invention comprise a FGRKMDR sequence (SEQ ID NO: 2). This sequence is comprised in the BNP(32) part of proBNP(1-108). Even more preferably, the fragments of proBNP(1-108) comprise the whole sequence of BNP(32) (SEQ ID NO: 3).

"Nucleoside Diphosphate kinase A (NDKA)" is well known to one of skill in the art and is notably described in Allard et al. (2005) Clin. Chem. 51:2043-2051. As intended herein "Nucleoside Diphosphate kinase A (NDKA)" encompasses all its natural variants, mutants, fragments, and the various glycosylated and phosphorylated forms thereof. By way of example NDKA is represented by SEQ ID NO: 5 and/or by Swissprot accession number P15531. Preferably, the above-defined natural variants or mutants of NDKA are such that they present at least 80%, more preferably at least 90% and most preferably at least 95% identity with SEQ ID NO: 5. As will be clear to one of skill in the art, are also within the scope of the invention methods according to the invention wherein the level of at least one further stroke marker is measured, kits according to the invention comprising antibodies to at least one further stroke marker and uses according to the invention of at least one further stroke marker. The expression "further stroke marker" relates to any biochemical marker, other than proBNP(1-108), fragments of proBNP(1-108) as defined above, or NDKA, which level is indicative of stroke or TIA as defined above.

The expression "marker of cardiovascular diseases" relates to any marker useful for detecting or diagnosing a cardiovascular diseases. Such markers are well known to one of skill in the art. Preferably, the marker of cardiovascular diseases is selected from the group constituted of the C reactive protein (CRP) and cardiac troponin I (cTnI). Measuring the level of a marker of cardiovascular diseases may be advantageous in the method of the invention since it enables excluding cardiovascular diseases as a cause for variation of the level of proBNP (1-108).

Preferably, measuring or determining the level of proBNP (1-108), of fragments of proBNP(1-108), of NDKA, of the at least one further stroke marker, or of the at least one marker of cardiovascular diseases is determined using an immunoassay.

As intended herein an "immunoassay" relates to any method wherein the level of proBNP(1-108), of fragments of proBNP(1-108), of NDKA, of the at least one further stroke marker, or of the at least one marker of cardiovascular diseases, is determined using at least one compound (or ligand) specifically binding thereto. The compound (or ligand) specifically binding thereto can be of any type but it is preferred that it is an antibody, an aptamer, or a peptide obtained by phage display. Immunoassay methods are well known to one of skill in the art and may be carried out in accordance with various formats well-known to the one skilled in the art, for example in solid or homogeneous phase, in one or two steps, by a sandwich method or by a competitive method.

Preferably, the sandwich method in solid phase between 2 ligands, one being a capture ligand and the other being a detection ligand, will be used. This type of immunoassay is particularly well-known to one skilled in the art. For example, the article by Seferian et al. (2007) Clin. Chem. 53:866-873 gives an example of a sandwich immunoassay (or immunometric assay at 2 sites) for assaying BNP(32) and proBNP(1-108), each time using a pair of antibodies (an antibody immobilised in solid phase and an labelled antibody in detection).

The presence of the antigen in the biological sample is revealed by detection means, in particular a "detection ligand". A detection ligand, which is labelled, is able to bind to the captured antigen, by recognising an epitopic site which is different from that recognised by the capture ligand.

The term "labelled" refers both to a direct labelling and to an indirect labelling (for example, by means of other ligands, themselves directly labelled, or using reagents of a labelled "affinity pair", such as, but not exclusively, the labelled avidin-biotin pair, etc.).

In the case of the sandwich method, the capture ligand is preferably selected in such a way that it specifically recognises an epitope on the natural antigen of the patient, whilst the detection ligand is selected preferably in such a way that it specifically recognises another epitope on the natural antigen of the patient.

Preferably, the capture ligand is immobilised on a solid phase. By way of non-limiting examples of solid phase, microplates could be used, in particular polystyrene microplates, such as those sold by Nunc, Denmark. Solid particles or beads, paramagnetic beads, such as those produced by Dynal, Merck-Eurolab (France) (under the trademark Estapor™) and Polymer Laboratories, or even polystyrene or polypropylene test tubes, glass, plastic or silicon chips, etc. may also be used.

ELISA assays, radioimmunoassays, or any other detection method may be used to reveal the presence of formed antigen-antibody complexes. Thus, different types of labelling of ligands in particular of antibodies, are possible (radioactive, ezymatic, fluorescent, etc.).

The detection may also be carried out by methods based on mass accumulation, such as surface plasmon resonance (SPR), by piezo-electric detection, but also by mass spectrometry or any other methods defined as enabling the study of a ligand-antigen-type interaction in the absence of a second labelled ligand.

The term "specific", when it refers to recognition of a ligand or binding of a ligand to a target, means that the ligand interacts with the target without interacting substantially with another target which does not structurally resemble the target.

An "antibody" as intended herein relates to antibodies belonging to any species, such as human, mouse, rat, rabbit, goat, or camelidae species. The antibody can also be a chimeric antibody, i.e. an antibody which comprises parts originating from different species. Preferred chimeric antibodies are so-called "humanized" antibodies, wherein the constant parts ($C_H$ and $C_L$) are of human origin and the variable parts ($V_H$ and $V_L$) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')$_2$, scFv fragments as well as camelidae single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) Nature 346:818-22 and Bock et al. (1992) Nature 355:564-6. The aptamers of a peptide nature and the production thereof are described, in particular, by Hoppe-Seyler et al. (2000) J. Mol Med. 78:426-30.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott & Smith (1990) Science 249:386-390, and Marks et al. (1991) J. Mol. Biol. 222:581-597. Preferably, the polypeptide obtainable by phage display is an scFv-type polypeptide (single-chain variable fragment). This technique is described, in particular, by Winter et al. (1994) Annu. Rev. Immunol. 12:433-455.

Preferably, the above-defined immunoassay comprises an antibody targeting an epitope which comprises the RAPRSP sequence (SEQ ID NO: 1). More preferably, the antibody is secreted by the hybridoma deposited at the CNCM (Collection Nationale de Cultures de Microorganismes, Institut Pasteur, 25, rue du Docteur Roux, 75 724 Paris Cedex 15, France) under the Budapest Treaty on Apr. 29, 2005, under reference number I-3073. Such an antibody is notably described in the international publication WO 2004/014952. This antibody is advantageous, in that it enables the specific detection of proBNP(1-108) and of all the fragments of proBNP(1-108) according to the invention, with the notable exception of BNP(32), NT-proBNP and their respective fragments, thereby ensuring obtaining the full diagnosis benefits of proBNP(1-108) and its various fragments.

Preferably also, the immunoassay comprises an antibody targeting an epitope which comprises the FGRKMDR sequence. More preferably, the antibody is secreted by the hybridoma deposited by Bio-Rad (3 boulevard Raymond Poincaré, 92430 Marnes la Coquette, France) at the CNCM (Collection Nationale de Cultures de Microorganismes, Institut Pasteur, 25, rue du Docteur Roux, 75 724 Paris Cedex 15, France) under the Budapest Treaty on Apr. 13, 2007, under reference number I-3746. Such an antibody is notably described in international application PCT/EP2008/060188.

Advantageously, the antibody targeting an epitope which comprises the RAPRSP sequence (SEQ ID NO: 1) and the antibody targeting an epitope which comprises the FGRKMDR sequence are combined in a same immunoassay, thereby enabling the specific detection of proBNP(1-108) or of fragments of proBNP(1-108) according to the invention.

Preferably, NDKA level is measured using an ELISA method as generally described in international application WO 2005/029088 and in Allard et al. (2005) Clin. Chem. 51:2043-2051.

Preferably, where proBNP(1-108), or of fragments of proBNP(1-108) are concerned, the cut-off value as defined above is of at least the mean level of proBNP(1-108), or of fragments of proBNP(1-108) according to the invention in biological samples obtained from an apparently healthy population of individuals. More preferably, the above-defined cut-off value is of at least the value corresponding to the 75th percentile, the 95th percentile, or the 99th percentile of the levels of proBNP(1-108), or of fragments of proBNP(1-108) according to the invention obtained from an apparently healthy population of individuals. Most preferably, this cut-off value is of at least 0, 1, 2, 3, 5, 10, 50 or 100 pg/ml. Where the cut-off value is of at least 0 pg/ml this means that the above defined steps a) and b) of the method of the invention consist simply in determining whether proBNP(1-108), or fragments of proBNP(1-108), as defined above are present in the biological sample of the individual.

Similarly, where NDKA is concerned, the cut-off value as defined above is preferably of at least the mean level of NDKA in biological samples obtained from an apparently healthy population of individuals. More preferably, the above-defined cut-off value is of at least the value corresponding to the 75th percentile, the 95th percentile, or the 99th percentile of the levels of NDKA obtained from an apparently healthy population of individuals. Most preferably, this cut-off value is of at least 5, 10, 15, or 20 ng/ml.

Similarly, where the at least further stroke marker is concerned, the cut-off value as defined above is preferably of at least the mean level of said at least one further stroke marker in biological samples obtained from an apparently healthy population of individuals.

It is well within the ordinary skills of one of skill in the art to determine cut-off values according to the invention. In particular, care should preferably taken to measure the level of proBNP(1-108), of fragments of proBNP(1-108) according to the invention, or of the at least one further stroke marker, in biological samples which are of the same nature. As intended herein, "an apparently healthy population of individuals" relates to individuals which preferably present none of the symptoms indicative of stroke as defined above.

Where the level of proBNP(1-108), or of fragments of proBNP(1-108), and the level of the at least one further stroke marker, are compared with one or several cut-off values, this means that the level of proBNP(1-108), or of fragments of proBNP(1-108), on one hand, and the level of the at least one further stroke marker, on the other hand, can be each compared to respective cut-off values, or that they can be both compared to a single cut-off value.

It is preferred that the level of NDKA (and optionally also that of the at least one further stroke marker or marker of cardiovascular diseases) is measured in the same biological sample as that in which the level of proBNP(1-108), or of fragments of proBNP(1-108), is measured.

As intended herein, the expression "biological sample" includes both the sample as taken and the sample which has been subjected to various treatments, in particular to render it suitable for use in the processes and methods according to the invention. The biological sample according to the invention can be of any type, however it is preferred that the biological sample is selected from the group constituted of a blood sample, a serum sample, a plasma sample, a cerebrospinal fluid sample, a urine sample and a saliva sample.

EXAMPLES

Example 1

1. Methods
a. Samples

The levels of proBNP(1-108) and NDKA were determined in 70 serum samples obtained from individuals in whom a stroke has occurred less than 3 hours after onset (15 hemorrhagic stroke samples (HM) and 55 ischemic stroke samples (IM)) and in 148 control serum samples from apparently healthy individuals.
b. Marker Level Determination The proBNP(1-108) level was determined using the BioPlex™ 2200 proBNP(1-108) assay (Bio-Rad).

The BioPlex™ 2200 combines multiplex, magnetic bead and flow cytometry technologies to provide multi-analyte detection on a fully automated random access platform. Magnetic particles (8 µm diameter, carboxyl-modified surface) are dyed with 2 fluorophores (classification dyes, CL1 and CL2) which emit at distinct wavelengths and adsorb significantly at 635 nm. The reporter fluorophore, β-phycoerythrin (PE) was chosen for its high molar extinction coefficient, quantum yield, resistance to photobleaching, lack of self-quenching and stability. The detector simultaneously measures light at 3 wavelengths: the 2 classification dyes and the reporter dye.

The BioPlex™ 2200 proBNP(1-108) assay is a two-step sandwich fluorescence immunoassay. In a first step, the BioPlex™ 2200 system combines 50 µL of patient sample, magnetic dyed beads coated with the anti-proBNP(1-108) monoclonal antibody secreted by the hybridoma deposited at the CNCM under reference number 1-3073 and assay buffer into a reaction vessel. Then, after 11 minutes of incubation and wash cycles, anti-human BNP monoclonal antibody secreted by the hybridoma deposited at the CNCM under reference number 1-3746 conjugated to phycoerythrin (PE) is added and incubated for 2 minutes. After removal of excess conjugate, the bead mixture is passed through the detector which identifies the dyed beads and the amount of antigens captured on the beads by the fluorescence of PE. After calibration using a set of 6 distinct calibrators, the 3 levels of quality controls and patient samples results are expressed in pg/mL.

Two Quality Control beads are also tested with each sample to enhance the integrity of the overall system.

The NDKA level was determined using an ELISA method as generally described in international application WO 2005/029088 and in Allard et al. (2005) Clin. Chem. 51:2043-2051.

c. Statistical Analysis

Distribution of biomarkers according to patient status was represented by boxplot representation, which is a convenient way of graphically depicting groups of numerical data through their five-number summaries (the smallest observation, lower quartile (Q1), median (Q2), upper quartile (Q3), and largest observation).

Data have been normalized using the Box-Cox method to follow a Gaussian distribution and enable statistical analysis (Box, G. E. P. and Cox, D. R. (1964) An analysis of transformations. JRSS B 26, 211-246).

Differential analysis between the control and stroke samples were done using the following statistical tests: the Wilcoxon Rank Sum Test (Wilcoxon, F. (1945). Individual comparisons by ranking methods. Biometrics, 1, 80-83) which is non-parametric (requires no assumption of statistical distribution and which can be an alternative to Student's t-test) and the Welch's test which is an adaptation of Student's t-test intended for use with two samples having possibly unequal variances. The analysis also includes the adjusted (corrected) versions of these tests by the Benjamini/Hochber method (Benjamini and Y. Hochberg (1995). Controlling the False Discovery Rate: a practical and powerful approach to multiple testing. J. R. Statist. Soc. B. Vol. 57: 289-300) was also performed.

The diagnostic performance of the markers was characterized by two indices: sensitivity (ability to detect the diseased population) and specificity (ability to detect the control population). The result of a diagnostic test can be further characterized by determining the area under the curve (AUC) of a ROC (receiver operating characteristic) analysis. The ROC curves are a graphical visualization of the reciprocal relation between the sensitivity (Se) and the specificity (Sp) of a test for various concentrations (M. H. Zweig and G. Campbell (1993). "Receiver-operating characteristic (ROC) plots: a fundamental evaluation tool in clinical medicine". Clinical chemistry 39 (8): 561-57).

Multivariate ROC curve analysis (mROC) was also performed for the proBNP (1-108) and NDKA marker combination, when comparing control to ischemic stroke patients and control to hemorrhagic stroke patients, using a mROC software well described by Kramar et al. (Comput. Methods Programs Biomed. 2001; 66:199-207; Revue d'Epidémiologie et Santé Publique 1999; 47:376-83).

mROC is a dedicated program calculating the linear combination (Su et al. Journal of the American Statistical Association 1993; 88:1350-1355), to maximize the AUC (Area Under the Curve) ROC for all markers selected (Staack et al. BMC Urology 2006; 6:1-12). The equation for the respective combination is provided and can be used as a new virtual marker. For a marker combination and for a sample selected, the cut-off is the result value of the linear equation corresponding and calculated by the mROC program:

Marker combination cut-off=$a \times$Marker1+$b \times$Marker2 where a and b are calculated coefficients and Marker1 and Marker2 are individual marker cut-off values.

2. Results a) Differential Analysis

The statistical significance of the difference in NDKA and proBNP(1-108) levels between stroke samples and control samples was determined:

TABLE 1

Differential analysis between concentrations determined from the Control and the Stroke populations for NDKA and proBNP markers

| Markers | pWILCOXbrut | pWILCOXadj | pWELCHbrut | pWELCHadj |
|---|---|---|---|---|
| proBNP | 1.00E−04 | 1.00E−04 | 1.00E−04 | 0.00012 |
| NDKA | 1.00E−04 | 1.00E−04 | 1.00E−04 | 0.00012 |

In this table, the difference in concentrations between the stroke samples and the control samples is statistically significant for both the proBNP and the NDKA markers are statistically significant with very low p-values ($10^{-4}$).

b) Univariate ROC Curve Analysis

The NDKA Marker

TABLE 2

Receiving-Operation-Characteristic analysis data for NDKA for Stroke patients when compared to Control subjects

| NDKA | Cut-off determined from normalized values | Se | Sp | AUC | IC 95% |
|---|---|---|---|---|---|
| Ctrl Vs Stroke | 1.507 | 90% | 92% | 0.958 | 0.913-0.980 |
| Ctrl Vs IM | 1.492 | 92% | 92% | 0.961 | 0.915-0.983 |
| Ctrl Vs HM | 1.085 | 90% | 85% | 0.943 | 0.859-0.978 |

The NDKA marker has a high discriminatory power in the prediction of stroke with a sensitivity of 90%, a specificity of 91.7% (Area Under the ROC curve (AUC): 0.952). Moreover, this discriminatory power is very high for both the ischemic and the hemorrhagic stroke patients compared to the control subjects.

The proBNP Marker

TABLE 3

Receiving-Operation-Characteristic analysis data for proBNP for Stroke patients when compared to Control subjects

| proBNP | Cut-off determined from normalized values | Se | Sp | AUC | IC 95% |
|---|---|---|---|---|---|
| Ctrl Vs Stroke | 0.717 | 88% | 94% | 0.952 | 0.885-0.981 |
| Ctrl Vs IM | 0.71 | 89% | 94% | 0.95 | 0.865-0.983 |
| Ctrl Vs HM | 0.659 | 90% | 94% | 0.962 | 0.500-0.998 |

The proBNP marker has a high discriminatory power in the prediction of cerebrovascular accident with a sensitivity of 88%, a specificity of 93.8% and an area under the ROC curve (AUC) of 0.952. Moreover, this discriminatory power is very high for both the ischemic and the hemorrhagic stroke patients compared to the control subjects with respective AUC of 0.95 and 0.962.

c) Multivariate ROC Curve Analysis
Control Versus Stroke

TABLE 4

Multivariate Receiving-Operation-Characteristic analysis data for the NDKA and proBNP combination for Stroke patients when compared to Control subjects

| Ctrl Vs Stroke | Cut-off determined from normalized values | Se | Sp | AUC | IC 95% |
|---|---|---|---|---|---|
| NDKA, proBNP | 4.1 | 93% | 100% | 0.99 | 0.975-0.996 |

Linear equations for decision rules: Z = 0.479*[proBNP] + 2.815*[NDKA]

The proBNP and NDKA combination has a high discriminatory power in the detection of stroke with a sensitivity of 93% at a specificity of 100%. Both, sensitivity and specificity are improved using this combination compared to each single analyte.

Control Versus Ischemic

TABLE 5

Multivariate Receiving-Operation-Characteristic analysis data for the NDKA and proBNP combination for Ischemic Stroke patients when compared to Control subjects

| Ctrl Vs Ischemic | Cut-off determined from normalized values | Se | Sp | AUC | IC 95% |
|---|---|---|---|---|---|
| NDKA, proBNP | 5.022 | 95% | 100% | 0.995 | 0.979-0.999 |

Linear equations for decision rules: Z = 3.782*[NDKA] + 0.526*[proBNP]

The proBNP and NDKA combination has a high discriminatory power in the detection of Ischemic stroke with a sensitivity of 95% at a specificity of 100%. Both, sensitivity and specificity are improved using this combination compared to each single analyte.

Control Versus Hemorrhagic

TABLE 6

Multivariate Receiving-Operation-Characteristic analysis data for the NDKA and proBNP combination for Hemorrhagic Stroke patients when compared to Control subjects

| Ctrl Vs HM | Cut-off determined from normalized values | Se | Sp | AUC | IC 95% |
|---|---|---|---|---|---|
| NDKA, proBNP | 6.589 | 95% | 98% | 0.993 | 0.962-0.999 |

Linear equations for decision rules: Z = 6.906*[NDKA] + 0.200*[proBNP]

The proBNP and NDKA combination has a high discriminatory power in the detection of hemorrhagic stroke with a sensitivity of 95% at a specificity of 98%. Both, sensitivity and specificity are improved using this combination compared to each single analyte.

The invention claimed is:

1. A method for the in vitro diagnosis of stroke and transient ischemic attack (TIA) in an individual, comprising the following steps:

(a) measuring the level of proBNP(1-108), or of fragments of proBNP(1-108) comprising a RAPRSP sequence (SEQ ID NO: 1), in a biological sample of the individual using an immunoassay, wherein the immunoassay comprises an antibody targeting an epitope which comprises the RAPRSP sequence (SEQ ID NO: 1);

(b) measuring the level of nucleoside diphosphate kinase A (NDKA) in a biological sample of the individual;

(c) comparing the level of proBNP(1-108), or of fragments of proBNP(1-108), and the level of NDKA, with one or several cut-off values; and (d) determining therefrom whether a stroke or a TIA has occurred in the individual.

2. The method according to claim 1, wherein the fragments of proBNP(1-108) further comprise a FGRKMDR sequence (SEQ ID NO: 2).

3. The method according to claim 1, wherein the fragments of proBNP(1-108) comprise the sequence of BNP(32) (SEQ ID NO: 3).

4. The method according to claim 1, wherein the stroke is selected from the group consisting of an ischemic stroke and a hemorrhagic stroke.

5. The method according to claim 1, wherein step (a) is implemented within 6 hours after the onset of at least one symptom indicative of stroke in the individual.

6. The method according to claim 1, wherein the antibody is secreted by the hybridoma deposited at the Collection Nationale de Cultures de Microorganismes (CNCM) (Paris, France) under the Budapest Treaty on Jul. 31, 2003, under reference number I-3073.

7. The method according to claim 1, wherein the immunoassay comprises an antibody targeting an epitope which comprises the FGRKMDR sequence (SEQ ID NO: 2).

8. The method according to claim 7, wherein the antibody is secreted by the hybridoma deposited at the CNCM (Paris, France) under the Budapest Treaty on Apr. 13, 2007, under reference number I-3746.

9. The method according to claim 1, wherein the NDKA level is measured using an immunoassay.

10. The method according to claim 1, wherein the level of NDKA is measured in the same biological sample as that in which the level of proBNP(1-108), or of fragments of proBNP(1-108), is measured.

11. The method according to claim 1, wherein the biological sample is selected from the group consisting of a blood sample, a serum sample, a plasma sample, a cerebrospinal fluid sample, a urine sample and a saliva sample.

12. The method according to claim 1, further comprising measuring the level of at least one marker of cardiovascular diseases.

13. The method according to claim 12, wherein the at least one marker of cardiovascular diseases is selected from the group consisting of CRP and cTnI.

14. A kit for diagnosing stroke or TIA, comprising:
at least one antibody suitable for detecting proBNP(1-108), or of fragment of proBNP(1-108) which comprise a RAPRSP sequence (SEQ ID NO: 1); and
at least one antibody suitable for detecting NDKA.

* * * * *